US009155302B2

(12) United States Patent
Suty-Heinze et al.

(10) Patent No.: US 9,155,302 B2
(45) Date of Patent: Oct. 13, 2015

(54) ACTIVE SUBSTANCE COMBINATIONS

(75) Inventors: Anne Suty-Heinze, Langenfeld (DE); Heike Hungenberg, Langenfeld (DE); Wolfgang Thielert, Odenthal (DE); Hans-Ludwig Elbe, Wuppertal (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 1373 days.

(21) Appl. No.: 11/912,773

(22) PCT Filed: Apr. 15, 2006

(86) PCT No.: PCT/EP2006/003487
§ 371 (c)(1),
(2), (4) Date: May 6, 2008

(87) PCT Pub. No.: WO2006/114212
PCT Pub. Date: Nov. 2, 2006

(65) Prior Publication Data
US 2008/0293566 A1    Nov. 27, 2008

(30) Foreign Application Priority Data

Apr. 28, 2005  (DE) .......................... 10 2005 019 713
May 13, 2005   (DE) .......................... 10 2005 022 147

(51) Int. Cl.
A01N 43/56         (2006.01)
(52) U.S. Cl.
CPC ...................................... A01N 43/56 (2013.01)
(58) Field of Classification Search
CPC ....... A01N 51/00; A01N 43/56; A01N 43/90; A01N 43/22; A01N 47/02; A01N 53/00; A01N 43/40
See application file for complete search history.

(56) References Cited

U.S. PATENT DOCUMENTS

| | | | |
|---|---|---|---|
| 2,758,115 A | 8/1956 | Lorenz et al. | |
| 3,264,177 A | 8/1966 | Kenaga et al. | |
| 3,309,266 A | 3/1967 | Magee et al. | |
| 4,245,432 A | 1/1981 | Dannelly | |
| 4,272,417 A | 6/1981 | Barke et al. | |
| 4,808,430 A | 2/1989 | Kouno | |
| 4,962,126 A | 10/1990 | Drabek | |
| 5,478,855 A | 12/1995 | Suzuki et al. | |
| 5,876,739 A | 3/1999 | Turnblad et al. | |
| 5,914,344 A | 6/1999 | Yoshikawa et al. | |
| 6,436,968 B1 | 8/2002 | Erdelen et al. | |
| 7,314,958 B2 | 1/2008 | Elbe et al. | |
| 7,358,214 B2 | 4/2008 | Dunkel et al. | |
| 7,538,073 B2 | 5/2009 | Elbe et al. | |
| 7,598,389 B2 | 10/2009 | Dunkel et al. | |
| 2003/0176428 A1 | 9/2003 | Schneidersmann et al. | |
| 2004/0204470 A1* | 10/2004 | Elbe et al. ................... | 514/406 |
| 2006/0128769 A1 | 6/2006 | Dunkel et al. | |
| 2007/0037858 A1 | 2/2007 | Dunkel et al. | |
| 2007/0060579 A1 | 3/2007 | Wachendorff-Neumann et al. | |
| 2007/0066673 A1 | 3/2007 | Dunkel et al. | |
| 2007/0072930 A1 | 3/2007 | Dunkel et al. | |
| 2007/0082877 A1 | 4/2007 | Dunkel et al. | |
| 2007/0142327 A1 | 6/2007 | Funke et al. | |
| 2007/0196406 A1 | 8/2007 | Dunkel et al. | |
| 2007/0203148 A1 | 8/2007 | Dunkel et al. | |
| 2007/0276022 A1 | 11/2007 | Dunkel et al. | |
| 2007/0293455 A1 | 12/2007 | Dunkel et al. | |
| 2008/0058389 A1 | 3/2008 | Dunkel et al. | |
| 2008/0064874 A1 | 3/2008 | Dunkel et al. | |
| 2008/0139389 A1 | 6/2008 | Kneen et al. | |
| 2008/0242708 A1 | 10/2008 | Dunkel et al. | |
| 2008/0255071 A1 | 10/2008 | Suty-Heinze et al. | |
| 2008/0269263 A1 | 10/2008 | Dahmen et al. | |
| 2009/0029858 A1 | 1/2009 | Fischer et al. | |
| 2009/0076113 A1 | 3/2009 | Dunkel et al. | |
| 2009/0105316 A1 | 4/2009 | Dunkel et al. | |
| 2009/0118346 A1 | 5/2009 | Dunkel et al. | |
| 2009/0209769 A1 | 8/2009 | Straub | |
| 2010/0029730 A1 | 2/2010 | Dunkel et al. | |
| 2010/0324101 A1 | 12/2010 | Ebbinghaus et al. | |
| 2011/0009267 A1 | 1/2011 | Suty-Heinze | |
| 2011/0045104 A1 | 2/2011 | Alig et al. | |
| 2011/0046194 A1 | 2/2011 | Alig et al. | |

FOREIGN PATENT DOCUMENTS

| | | |
|---|---|---|
| CA | 1 082205 | 7/1980 |
| CA | 2 543 053 | 5/2005 |
| DE | 26 41 343 A1 | 4/1977 |
| EP | 0 210 487 A1 | 2/1987 |
| EP | 0 234 045 A2 | 9/1987 |
| EP | 0 347 488 A1 | 12/1989 |
| GB | 1181657 | 2/1970 |

(Continued)

OTHER PUBLICATIONS

Colby, S.R., "Calculating Synergistic and Antagonistic Responses of Herbicide Combinations," Weeds 15:20-22 (1967).
Ugerer, H.R., "Marine paints: a specialty of the (German) coastal paint industry," Chem. Ind. 37:730-732, Society of Chemical Industry, Translated in English by RWS Translations, London (1985).
International Search Report for International Application No. PCT/EP2006/003487, European Patent Office, Netherlands, mailed on Apr. 16, 2007.
Database CAPLUS on STN, Chemical Accession No. 2001:191978, English language abstract for Japanese Patent No. 2001072508.
Database CAPLUS on STN, Chemical Accession No. 2001:191977, English language abstract for Japanese Patent No. 2001072507.

(Continued)

Primary Examiner — Abigail Fisher
Assistant Examiner — Jessica Kassa
(74) Attorney, Agent, or Firm — Sterne, Kessler, Goldstein & Fox PLLC

(57) ABSTRACT

The present invention relates to novel active compound combinations comprising, firstly, known carboxamides and, secondly, insecticidally active compounds, which active compound combinations are highly suitable for controlling unwanted animal pests, such as insects or acarids, and also unwanted phytopathogenic fungi.

25 Claims, No Drawings

(56) References Cited

FOREIGN PATENT DOCUMENTS

| JP | 10-251240 A | 9/1998 |
|---|---|---|
| WO | WO 93/10083 A1 | 5/1993 |
| WO | WO 93/22297 A1 | 11/1993 |
| WO | WO 96/37494 A1 | 11/1996 |
| WO | WO 98/25923 A1 | 6/1998 |
| WO | WO 99/65313 A1 | 12/1999 |
| WO | WO 02/28186 A2 | 4/2002 |
| WO | WO 02/080675 A1 | 10/2002 |
| WO | WO 03/010149 A1 | 2/2003 |
| WO | WO 2004/005242 A1 | 1/2004 |
| WO | WO 2004/067515 A1 | 8/2004 |
| WO | WO 2005/034628 A1 | 4/2005 |
| WO | WO 2005/041653 A2 | 5/2005 |
| WO | WO 2005/077901 A2 | 8/2005 |
| WO | WO 2006/032356 A1 | 3/2006 |
| WO | WO 2006/105889 A2 | 10/2006 |

OTHER PUBLICATIONS

Database CAPLUS on STN, Chemical Accession No. 2001:194736, English language abstract for Japanese Patent No. 2001072510.
Co-pending Application, U.S. Appl. No. 10/581,348, inventors Funke et al., international filing date Nov. 20, 2004.
Co-pending Application, U.S. Appl. No. 11/910,659, inventors Wachendorff-Neumann et al., international filing date Mar. 27, 2007.
Rummens, F.H.A., "An Improved Definition of Synergistic and Antagonistic Effects," Weed Science 23(1):4-6, The Weed Science Society of America, United States (1975).
Office Action mailed Mar. 10, 2011, in U.S. Appl. No. 11/629,982, Keen et al., filed Nov. 1, 2007.
Office Action mailed Mar. 9, 2011, in U.S. Appl. No. 12/831,990, Suty-Heinze et al., filed Jul. 7, 2010.
Bauer, T.A., et al., "Response of Selected Weed Species to Postemergence Imazethapyr and Bentazon," Weed Tech. 9:236-242, The Weed Science Society of America, United States (1995).
Blackshaw, R.E., "HOE-39866 Use in Chemical Fallow Systems," Weed Tech. 3:420-428, The Weed Science Society of America, United States (1989).
Blackshaw, R.E., "Synergistic Mixes of DPX-A7881 and Clopyralid in Canola (Brassica napus)," Weed Tech. 3:690-695, The Weed Science Society of America, United States (1989).
Blackshaw, R.E. et al., "Herbicide Combinations for Postemergent Weed Control in Safflower (Carthamus tinctorius)," Weed Tech. 4:97-104, The Weed Science Society of America, United States (1990).
Blouin, D.C., et al., "Analysis of Synergistic and Antagonistic Effects of Herbicides Using Nonlinear Mixed-Model Methodology," Weed Tech. 18:464-472, The Weed Science Society of America, United States (2004).
Bradley, P.R., et al., "Response of Sorghum (Sorghum bicolor) to Atrazine, Ammonium Sulfate, and Glyphosate," Weed Tech. 14:15-18, The Weed Science Society of America, United States (2000).
Buker, III, R.S., et al., "Confirmation and Control of a Paraquat-Tolerant Goosegrass (Eleusine indica) Biotype," Weed Tech. 16:309-313, The Weed Science Society of America, United States (2002).
Burke, I.C., et al., "CGA-362622 Antagonizes Annual Grass Control with Clethodim," Weed Tech. 16:749-754, The Weed Science Society of America, United States (2002).

Flint, J.L., et al., "Analyzing Herbicide Interactions, A Statistical Treatment of Colby's Method," Weed Tech. 2:304-309, The Weed Science Society of America, United States (1988).
Gillespie, G.R., and Nalewaja, J.D., "Wheat (Triticum aestivum) Response to Triallate Plus Chlorsulfuron," Weed Tech. 3:20-23, The Weed Science Society of America, United States (1989).
Green, J.M., et al., "Metribuzin and Chlorimuron Mixtures for Preemergence Broadleaf Weed Control in Soybeans, Glycine max," Weed Tech. 2:355-363, The Weed Science Society of America, United States (1988).
Harker, N.K., and O'Sullivan, P.A., "Synergistic Mixtures of Sethoxydim and Fluazifop on Annual Grass Weeds," Weed Tech. 5:310-316, The Weed Science Society of America, United States (1991).
Kent, L.M., et al., "Effect of Ammonium Sulfate, Imazapyr, and Environment on the Phytotoxicity of Imazethapyr," Weed Tech. 5:202-205, The Weed Science Society of America, United States (1991).
Kotoula-Syka, E., et al., "Interactions between SAN 582H and Selected Safeners on Grain Sorghum (Sorghum bicolor) and Corn (Zea mays)," Weed Tech. 10:299-304, The Weed Science Society of America, United States (1996).
Lanclos, D.Y., et al., "Glufosinate Tank-Mix Combinations in Glufosinate-Resistant Rice (Oryza sativa)," Weed Tech. 16:659-663, The Weed Science Society of America, United States (2002).
Norris, J.L., et al., "Weed Control from Herbicide Combinations with Three Formulations of Glyphosate," Weed Tech. 15:552-558, The Weed Science Society of America, United States (2001).
Novosel, K.M., et al., "Metolachlor Efficacy as Influenced by Three Acetolactate Synthase-Inhibiting Herbicides," Weed Tech. 12:248-253, The Weed Science Society of America, United States (1998).
Palmer, E.W., et al., "Broadleaf Weed Control in Soybean (Glycine max) with CGA-277476 and Four Postemergence Herbicides," Weed Tech. 14:617-623, The Weed Science Society of America, United States (2000).
Salzman, F.P., and Renner, K.A., "Response of Soybean Combinations of Clomazone, Metribuzin, Linuron, Alachlor, and Atrazine," Weed Tech. 6:922-929, The Weed Science Society of America, United States (1992).
Scott, R.C., et al., "Spray Adjuvant, Formulation, and Environmental Effects of Synergism from Post-Applied Tank Mixtures of SAN 582H with Fluazifop-P, Imazethapyr, and Sethoxydim," Weed Tech. 12:463-469, The Weed Science Society of America, United States (1998).
Shaw, D.R. and Arnold, J.C., "Weed Control from Herbicide Combinations with Glyphosate," Weed Tech. 16:1-6, The Weed Science Society of America, United States (2002).
Snipes, C.E., and Allen, R.L., "Interaction of Graminicides Applied in Combination with Pyrithiobac," Weed Tech. 10:889-892, The Weed Science Society of America, United States (1996).
Wehtje, G. and Walker, R.H., "Interaction of Glyphosate and 2,4-DB for the Control of Selected Morningglory (Ipomoea spp.) Species," Weed Tech. 11:152-156, The Weed Science Society of America, United States (1997).
Zhang, W., et al., "Fenoxaprop Interactions for Barnyardgrass (Echinochloa crus-galli) Control in Rice," Weed Tech. 19:293-297, The Weed Science Society of America, United States (2005).
Office Action mailed Aug. 29, 2011, in U.S. Appl. No. 11/629,982, Kneen et al., §371 (c) date Nov. 1, 2007.

\* cited by examiner

ACTIVE SUBSTANCE COMBINATIONS

This application is a National Stage of International Application No. PCT/EP2006/003487, filed Apr. 15, 2006, which claims the benefit of German Patent Application No. 102005019713.2, filed Apr. 28, 2005, and German Patent Application No. 102005022147.5, filed May 13, 2005 The entirety of each of these applications is incorporated by reference herein.

The present invention relates to novel active compound combinations comprising, firstly, known carboxamides and, secondly, insecticidally active compounds, which active compound combinations are highly suitable for controlling unwanted animal pests, such as insects or acarids, and also unwanted phytopathogenic fingi.

It is already known that certain carboxamides have fungicidal properties: for example N-[2-(1,3-dimethylbutyl)phenyl]-5-fluoro-1,3-dimethyl-1H-pyrazole-4-carboxamide from WO 03/010149 und 3-(trifluoromethyl)-N-[2-(1,3-dimethylbutyl)phenyl]-5-fluoro-1-methyl-1H-pyrazole-4-carboxamide from DE-A 103 03 589. The activity of these compounds is good; however, at low application rates it is sometimes unsatisfactory.

Furthermore, it is known that numerous phosphoric esters, carbamates, heterocycles, organotin compounds, benzoylureas and pyrethroids have insecticidal and acaricidal properties (cf, for example, U.S. Pat. No. 2,758,115, U.S. Pat. No. 3,309,266, GB 1,181,657, WO 93/22297 A1, WO 93/10083 A1, DE2641 343 A1, EP 347 488 A1, EP 210 487 A1, U.S. Pat. No. 3,264,177 and EP 234 045 A2). However, the activity of these compounds is likewise not always satisfactory.

This invention now provides novel active compound combinations having very good fungicidal, insecticidal and/or acaricidal properties, comprising a carboxamide of the general formula (I) (group 1)

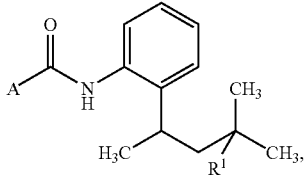
(I)

in which
R¹ represents hydrogen, halogen, $C_1$-$C_3$-alkyl or $C_1$-$C_3$-haloalkyl having 1 to 7 fluorine, chlorine and/or bromine atoms,
A represents one of the radicals A1 to A8 below:

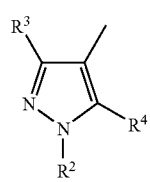
A1

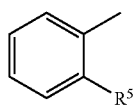
A2

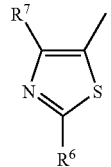
A3

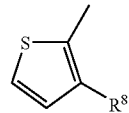
A4

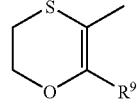
A5

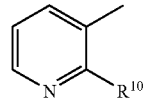
A6

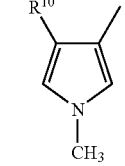
A7

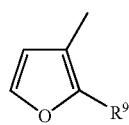
A8

$R^2$ represents $C_1$-$C_3$-alkyl,
$R^3$ represents hydrogen, halogen, $C_1$-$C_3$-alkyl or $C_1$-$C_3$-haloalkyl having 1 to 7 fluorine, chlorine and/or bromine atoms,
$R^4$ represents hydrogen, halogen or $C_1$-$C_3$-alkyl,
$R^5$ represents halogen, $C_1$-$C_3$-alkyl or $C_1$-$C_3$-haloalkyl having 1 to 7 fluorine, chlorine and/or bromine atoms,
$R^6$ represents hydrogen, halogen, $C_1$-$C_3$-alkyl, amino, mono- or di($C_1$-$C_3$-alkyl)amino,
$R^7$ represents hydrogen, halogen, $C_1$-$C_3$-alkyl or $C_1$-$C_3$-haloalkyl having 1 to 7 fluorine, chlorine and/or bromine atoms,
$R^8$ represents halogen, $C_1$-$C_3$-alkyl or $C_1$-$C_3$-haloalkyl having 1 to 7 fluorine, chlorine and/or bromine atoms,
$R^9$ represents halogen, $C_1$-$C_3$-alkyl or $C_1$-$C_3$-haloalkyl having 1 to 7 fluorine, chlorine and/or bromine atoms,
$R^{10}$ represents hydrogen, halogen, $C_1$-$C_3$-alkyl or $C_1$-$C_3$-haloalkyl having 1 to 7 fluorine, chlorine and/or bromine atoms,
and at least one active compound selected from groups (2) to (24) below:
group (2) acetylcholine receptor agonists/antagonists (preferably chloronicotinyl/neonicotinoids);
group (3) acetylcholinesterase (AChE) inhibitors (preferably carbamates and organophosphates);
group (4) sodium channel modulators/voltage-gated sodium channel blockers (preferably pyrethroids and oxadiazines);
group (5) acetylcholine receptor modulators (preferably spinosyns);
group (6) GABA-gated chloride channel antagonists (preferably cyclodiene organochlorines and fiproles);

group (7) chloride channel activators (preferably mectins);
group (8) juvenile hormone mimetics;
group (9) ecdysone agonists/disruptors (preferably diacylhydrazines);
group (10) inhibitors of chitinbiosynthesis (preferably benzoylureas);
group (11) inhibitors of oxidative phosphorylation, ATP disruptors (preferably organotins);
group (12) decouplers of oxidative phosphorylation by disruption of the H proton gradient (preferably pyrroles and dinitrophenols);
group (13) site I electron transport inhibitors (preferably METIs);
group (14) site II electron transport inhibitors;
group (15) site III electron transport inhibitors;
group (16) microbial disrupters of the intestinal membrane of insects;
group (17) inhibitors of lipid synthesis (preferably tetronic acids and tetramic acids);
group (18) carboxamides;
group (9) octopaminergic agonists;
group (20) inhibitors of the magnesium-stimulated ATPase;
group (21) phthalamides;
group (22) nereistoxin analogues;
group (23) biologics, hormones or pheromones;
group (24) active compounds having unknown or non-specified mechanisms of action (preferably fumigants, selective feeding inhibitors and mite growth inhibitors).

Surprisingly, the fungicidal, insecticidal and/or acaricidal activity of the active compound combinations according to the invention is considerably higher than the sum of the activities of the individual active compounds. Thus, an unforeseeable synergistic effect is present, and not just an addition of activities.

The active compound combinations according to the invention comprise, in addition to at least one carboxamide of the general formula (I) (group 1), at least one active compound selected from groups (2) to (24).

The formula (I) provides a general definition of the compounds of group (1). The active compound combinations according to the invention preferably comprise a carboxamide of the general formula (I) in which the radicals are as defined below.

Preference is given to carboxamides of the formula (I) in which
$R^1$ represents hydrogen, fluorine, chlorine, methyl, ethyl, n-propyl, isopropyl, monofluoromethyl, difluoromethyl, trifluoromethyl, monochloromethyl, dichloromethyl or trichloromethyl,
A represents one of the radicals A1 to A5 below:

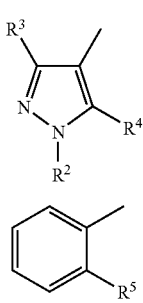

A1

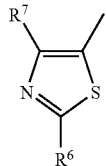

A2

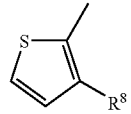

A3

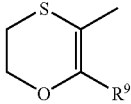

A4

A5

$R^2$ represents methyl, ethyl, n- or isopropyl,
$R^3$ represents iodine, methyl, difluoromethyl or trifluoromethyl,
$R^4$ represents hydrogen, fluorine, chlorine or methyl,
$R^5$ represents chlorine, bromine, iodine, methyl, difluoromethyl or trifluoromethyl,
$R^6$ represents hydrogen, chlorine, methyl, amino or dimethylamino,
$R^7$ represents methyl, difluoromethyl or trifluoromethyl,
$R^8$ represents bromine or methyl,
$R^9$ represents methyl or trifluoromethyl.

Particular preference is given to carboxamides of the formula (I) in which
$R^1$ represents hydrogen, fluorine, chlorine, methyl, ethyl or trifluoromethyl,
A represents one of the radicals A1 or A2 below:

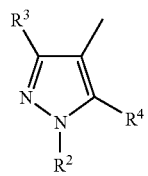

A1

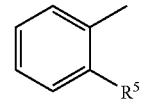

A2

$R^2$ represents methyl or isopropyl,
$R^3$ represents methyl, difluoromethyl or trifluoromethyl,
$R^4$ represents hydrogen or fluorine,
$R^5$ represents iodine, difluoromethyl or trifluoromethyl.

Very particular preference is given to carboxamides of the formula (I) in which
$R^1$ represents hydrogen or methyl,
A represents one of the radicals A1 or A2 below:

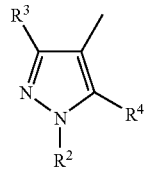

A1

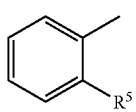
A2

R² represents methyl,
R³ represents methyl,
R⁴ represents fluorine,
R⁵ represents iodine or trifluoromethyl.

Very particular preference is given to using, in mixtures, compounds of the formula (Ia)

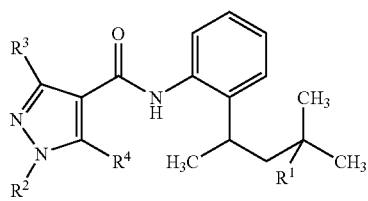
(Ia)

in which R¹, R², R³ and R⁴ are as defined above.

Very particular preference is given to using, in mixtures, compounds of the formula (Ib)

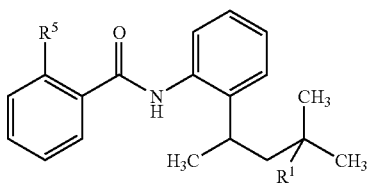
(Ib)

in which R¹ and R⁵ are as defined above.

The formula (I) embraces in particular the following preferred mixing partners of group (1):

(1-1) N-[2-(1,3-dimethylbutyl)phenyl]-1,3-dimethyl-1H-pyrazole-4-carboxamide
(1-2) N-[2-(1,3-dimethylbutyl)phenyl]-5-fluoro-1,3-dimethyl-1H-pyrazole-4-carboxamide (known from WO 03/010149)
(1-3) N-[2-(1,3-dimethylbutyl)phenyl]-5-chloro-1,3-dimethyl-1H-pyrazole-4-carboxamide (known from JP-A 10-251240)
(1-4) 3-(difluoromethyl)-N-[2-(1,3-dimethylbutyl)phenyl]-1-methyl-1H-pyrazole-4-carboxamide
(1-5) 3-(trifluoromethyl)-N-[2-(1,3-dimethylbutyl)phenyl]-5-fluoro-1-methyl-1H-pyrazole-4-carboxamide (known from DE-A 103 03 589)
(1-6) 3-(trifluoromethyl)-N-[2-(1,3-dimethylbutyl)phenyl]-5-chloro-1-methyl-1H-pyrazole-4-carboxamide (known from JP-A 10-251240)
(1-7) 1,3-dimethyl-N-[2-(1,3,3-trimethylbutyl)phenyl]-1H-pyrazole-4-carboxamide (known from JP-A 10-251240)
(1-8) 5-fluoro-1,3-dimethyl-N-[2-(1,3,3-trimethylbutyl)phenyl]-1H-pyrazole-4-carboxamide (known from WO 03/010149)
(1-9) 3-(difluoromethyl)-1-methyl-N-[2-(1,3,3-trimethylbutyl)phenyl]-1H-pyrazole-4-carboxamide
(1-10) 3-(trifluoromethyl)-1-methyl-N-[2-(1,3,3-trimethylbutyl)phenyl]-1H-pyrazole-4-carboxamide
(1-11) 3-(trifluoromethyl)-5-fluoro-1-methyl-N-[2-(1,3,3-trimethylbutyl)phenyl]-1H-pyrazole-4-carboxamide (known from DE-A 103 03 589)
(1-12) 3-(trifluoromethyl)-5-chloro-1-methyl-N-[2-(1,3,3-trimethylbutyl)phenyl]-1H-pyrazole-4-carboxamide (known from JP-A 10-251240)
(1-13) N-[2-(1,3-dimethylbutyl)phenyl]-2-iodobenzamide (known from DE-A 102 29 595)
(1-14) 2-iodo-N-[2-(1,3,3-trimethylbutyl)phenyl]benzamide (known from DE-A 102 29 595)
(1-15) N-[2-(1,3-dimethylbutyl)phenyl]-2-(trifluoromethyl)benzamide (known from DE-A 102 29 595)
(1-16) 2-(trifluoromethyl)-N-[2-(1,3,3-trimethylbutyl)phenyl]benzamide (known from DE-A 102 29 595)

Emphasis is given to active compound combinations according to the invention which, in addition to the carboxatyide (1-8) 5-fluoro-1,3-dimethyl-N-[2-(1,3,3-trimethylbutyl)phenyl]-1H-pyrazole-4-carbox-amide (group 1) comprise one or more, preferably one, mixing partner of groups (2) to (24).

Emphasis is given to active compound combinations according to the invention which, in addition to the carboxamide (1-2) N-[2-(1,3-dimethylbutyl)phenyl]-5-fluoro-1,3-dimethyl-1H-pyrazole-4-carboxamide (group 1) comprise one or more, preferably one, mixing partner of groups (2) to (24).

Emphasis is given to active compound combinations according to the invention which, in addition to the carboxamide (1-15) N-[2-(1,3-dimethylbutyl)phenyl]-2-(trifluoromethyl)benzamide (group 1) comprise one or more, preferably one, mixing partner of groups (2) to (24).

Emphasis is given to active compound combinations according to the invention which, in addition to the carboxamide (1-13) N-[2-(1,3-dimethylbutyl)phenyl]-2-iodobenzamide (group 1) comprise one or more, preferably one, mixing partner of groups (2) to (24).

The active compounds of groups (2) to (24) comprise a large number of possible mixing partners listed below.

Group (2) of the acetylcholine receptor agonist/antagonists comprises specifically the following active compounds:
(2.1) chloronicotinyls/neonicotinoids (for example acetamiprid, clothianidin, dinotefuran, imidacloprid, nitenpyram, nithiazine, thiacloprid, thiamethoxam);
(2.2) nicotine, bensultap, cartap.

The active compound combinations according to the invention preferably comprise the following acetylcholine receptor agonists/antagonists of group (2):
(2.1.1) clothianidin
(2.1.2) imidacloprid
(2.1.3) thiacloprid
(2.1.4) thiamethoxam
(2.1.5) acetamiprid
(2.1.6) dinotefuran
(2.1.7) nitenpyram The active compound combinations according to the invention particularly preferably comprise the following acetylcholine receptor agonists/antagonists of group (2):
(2.1.1) clothianidin
(2.1.2) imidacloprid
(2.1.3) thiacloprid
(2.1.4) thiamethoxam Group (3) of the acetylcholine esterase (AChE) inhibitors comprises specifically the following active compounds:
(3.1) carbamates (for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb);

(3.2) organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion).

The active compound combinations according to the invention preferably comprise the following acetylcholine esterase (AChE) inhibitors of group (3):
(3.1.1) methiocarb
(3.1.2) thiodicarb
(3.1.3) ethiofencarb
(3.1.4) aldicarb
(3.1.5) propoxur
(3.2.1) azinphos-methyl
(3.2.2) azinphos-ethyl
(3.2.3) phoxim
(3.2.4) prothiophos The active compound combinations according to the invention particularly preferably comprise the following acetylcholine esterase (AChE) inhibitors of group (3):
(3.1.1) methiocarb
(3.1.2) thiodicarb
(3.1.3) ethiofencarb
(3.2.1) azinphos-methyl
(3.2.2) azinphos-ethyl Group (4) of the sodium channel modulators/voltage-gated sodium channel blockers comprises specifically the following active compounds:
(4.1) pyrethroids [for example acrinathrin, allethrin (d-cis-trans, d-trans), beta-cyfluthrin, bifenthrin, bio-allethrin, bio-allethrin-S-cyclopentyl-isomer, bioethanomethrin, biopermethrin, bioresmethrin, chlovaporthrin, cis-cypermethrin, cis-resmethrin, cis-permethrin, clocythrin, cyloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, teralethrin, tetramethrin (1R-isomer), tralocythrin, tralomethrin, transfluthrin, ZXI 8901, pyrethrins (pyrethrum)];

(4.2) oxadiazines (for example indoxacarb).

The active compound combinations according to the invention preferably comprise the following sodium channel modulators/voltage-gated sodium channel blockers of group (4):
(4.1.1) beta-cyfluthrin
(4.1.2) cyfluthrin
(4.1.3) deltamethrin
(4.1.4) tau-fluvalinate
(4.1.5) eflusilanate
(4.2.1) indoxacarb The active compound combinations according to the invention particularly preferably comprise the following sodium channel modulators/voltage-gated sodium channel blockers of group (4):
(4.1.1) beta-cyfluthrin
(4.1.2) cyfluthrin
(4.1.3) deltamethrin
(4.1.4) tau-fluvalinate
(4.2.1) indoxacarb Group (5) of the acetylcholine receptor modulators comprises specifically the following active compounds:
(5.1) spinosyns (for example spinosad).

The active compound combinations according to the invention preferably comprise the following acetylcholine receptor modulator of group (5):
(5.1.1) spinosad Group (6) of the GABA-gated chloride channel antagonist comprises specifically the following active compounds:
(6.1) cyclodiene organochlorines (for example camphechlor, chlordane, endosulfan, gamma-HCH, HCH, heptachlor, lindane, methoxychlor);
(6.2) fiproles (for example acetoprole, ethiprole, fipronil, vaniliprole).

The active compound combinations according to the invention preferably comprise the following GABA-gated chloride channel antagonists of group (6):
(6.1.1) endosulfan
(6.2.1) fipronil
(6.2.2) ethiprole Group (7) of the chloride channel activators comprises specifically the following active compounds: (7.1) mectins (for example abamectin, avermectin, emamectin, emamectin-benzoate, ivermectin, milbemectin, milbemycin).

The active compound combinations according to the invention preferably comprise the following chloride channel activator of group (7):
(7.1.1) emamectin-benzoate Group (8) of the juvenile hormone mimetics comprises specifically the following active compounds: diofenolan, epofenonane, fenoxycarb, hydroprene, kinoprene, methoprene, pyriproxifen, triprene.

The active compound combinations according to the invention preferably comprise the following juvenile hormone mimetic of group (8):
(8.1.1) pyriproxifen Group (9) of the ecdysone agonists/disrupters comprises specifically the following active compounds:
(9.1) diacylhydrazines (for example chromafenozide, halofenozide, methoxyfenozide, tebufenozide).

The active compound combinations according to the invention preferably comprise the following ecdysone agonists/disrupters group (9):
(9.1.1) methoxyfenozide Group (10) of the inhibitors of chitin biosynthesis comprises specifically the following active compounds:
(10.1) benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron);
(10.2) buprofezin;
(10.3) cyromazine.

The active compound combinations according to the invention preferably comprise the following inhibitors of chitin biosynthesis of group (10):
(10.1.1) triflumuron
(10.1.2) flufenoxuron Group (11) of the inhibitors of the oxidative phosphorylation, ATP disruptors comprises specifically the following active compounds:
(11.1) diafenthiuron;
(11.2) organotin (for example azocyclotin, cyhexatin, fenbutatin oxide).

Group (12) of the decouplers of oxidative phosphorylation by disruption of the H proton gradient comprises specifically the following active compounds:
(12.1) pyrroles (for example chlorfenapyr);
(12.2) dinitrophenols (for example binapacyrl, dinobuton, dinocap, DNOC).

Group (13) of the site I electron transport inhibitors comprises specifically the following active compounds:
(13.1) METIs (for example fenazaquin, fenpyroximate, pyrimidifen, pyridaben, tebufenpyrad, tolfenpyrad);
(13.2) hydramethylnone;
(13.3) dicofol.

The active compound combinations according to the invention preferably comprise the following site I electron transport inhibitors of group (13):
(13.1.1) tebufenpyrad
(13.2.1) hydramethylone Group (14) of the site (H) electron transport inhibitors comprises specifically the following active compound:
(14.1.1) rotenone Group (15) of the site M electron transport inhibitors comprises specifically the following active compounds:
(15.1) acequinocyl, fluacrypyrim.

Group (16) of the microbial disrupters of the intestinal membrane of insects comprises specifically the following active compounds:
(16.1) *Bacillus thuringiensis* strains.

Group (17) of the inhibitors of lipid synthesis comprises specifically the following active compounds:
(17.1) tetronic acids (for example spirodiclofen, spiromesifen);
(17.2) tetramic acids {for example 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS reg. No.: 203313-25-1)}.

The active compound combinations according to the invention preferably comprise the following inhibitors of lipid synthesis of group (17):
(17.1.1) spirodiclofen
(17.1.2) spiromesifen
(17.2.1) 3-(2,5-dimethylphenyl)-8-methoxy-2-oxo-1-azaspiro[4.5]dec-3-en-4-yl ethyl carbonate Group (18) of the carboxamides comprises specifically the following active compound:
(18.1.1) flonicamid Group (19) of the octopaminergic agonists comprises specifically the following active compound:
(19.1.1) amitraz Group (20) of the inhibitors of the magnesium-stimulated ATPase comprises specifically the following active compound:
(20.1.1) propargite Group (21) of the phthalamides comprises specifically the following active compound:
(21.1.1) $N^2$-[1,1-dimethyl-2-(methylsulphonyl)ethyl]-3-iodo-N'-[2-methyl-4-[1,2,2,2-tetrafluoro-1-(trifluoromethyl)ethyl]phenyl]-1,2-benzenedicarboxamide (i.e. flubendiamide, CAS reg. No.: 272451-65-7).

Group (22) of the nereistoxin analogues comprises specifically the following active compounds: thiocyclam hydrogen oxalate, thiosultap-sodium.

Group (23) of the biologics, hormones or pheromones comprises specifically the following active compounds:
azadirachtin, *Bacillus* spec., *Beauveria* spec., codlemone, *Metarrhizium* spec., *Paecilomyces* spec., thuringiensin, *Verticillium* spec.

Group (24) of the active compounds having unknown or non-specific mechanisms of action comprises specifically the following active compounds:
(24.1) fumigants (for example aluminium phosphide, methyl bromide, sulphuryl fluoride);
(24.2) selective feeding inhibitors (for example cryolite, flonicamid, pymetrozine);
(24.3) mite growth inhibitors (for example clofentezine, etoxazole, hexythiazox);
(24.4) amidoflumet, benclothiaz, benzoximate, bifenazate, bromopropylate, buprofezin, chinomethioat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS reg. No. 185982-80-3) and the corresponding 3-endo isomer (CAS reg. No. 185984-60-5) (cf. WO 96/37494, WO 98/25923), and also preparations comprising insecticidal effective plant extracts, nematodes, fungi or viruses.

Particularly preferred combinations according to the invention are shown in the table below.

TABLE 1

| Active compound of group (1) | Active compound of groups (2) to (24) |
|---|---|
| (1-8) 5-fluoro-1,3-dimethyl-N-[2-(1,3,3-trimethylbutyl)phenyl]-1H-pyrazole-4-carboxamide | (2.1.1) clothianidin |
| (1-8) 5-fluoro-1,3-dimethyl-N-[2-(1,3,3-trimethylbutyl)phenyl]-1H-pyrazole-4-carboxamide | (2.1.2) imidacloprid |
| (1-8) 5-fluoro-1,3-dimethyl-N-[2-(1,3,3-trimethylbutyl)phenyl]-1H-pyrazole-4-carboxamide | (2.1.3) thiacloprid |
| (1-8) 5-fluoro-1,3-dimethyl-N-[2-(1,3,3-trimethylbutyl)phenyl]-1H-pyrazole-4-carboxamide | (2.1.4) thiamethoxam |

TABLE 1-continued

| Active compound of group (1) | Active compound of groups (2) to (24) |
|---|---|
| (1-8) 5-fluoro-1,3-dimethyl-N-[2-(1,3,3-trimethyl-butyl)phenyl]-1H-pyrazole-4-carboxamide | (3.1.1) methiocarb |
| (1-8) 5-fluoro-1,3-dimethyl-N-[2-(1,3,3-trimethyl-butyl)phenyl]-1H-pyrazole-4-carboxamide | (3.1.2) thiodoicarb |
| (1-8) 5-fluoro-1,3-dimethyl-N-[2-(1,3,3-trimethyl-butyl)phenyl]-1H-pyrazole-4-carboxamide | (3.1.3) ethiofencarb |
| (1-8) 5-fluoro-1,3-dimethyl-N-[2-(1,3,3-trimethyl-butyl)phenyl]-1H-pyrazole-4-carboxamide | (3.2.1) azinphos-methyl |
| (1-8) 5-fluoro-1,3-dimethyl-N-[2-(1,3,3-trimethyl-butyl)phenyl]-1H-pyrazole-4-carboxamide | (3.2.2) azinphos-ethyl |
| (1-8) 5-fluoro-1,3-dimethyl-N-[2-(1,3,3-trimethyl-butyl)phenyl]-1H-pyrazole-4-carboxamide | (4.1.1) beta-cyfluthrin |
| (1-8) 5-fluoro-1,3-dimethyl-N-[2-(1,3,3-trimethyl-butyl)phenyl]-1H-pyrazole-4-carboxamide | (4.1.2) cyfluthrin |
| (1-8) 5-fluoro-1,3-dimethyl-N-[2-(1,3,3-trimethyl-butyl)phenyl]-1H-pyrazole-4-carboxamide | (4.1.3) deltamethrin |
| (1-8) 5-fluoro-1,3-dimethyl-N-[2-(1,3,3-trimethyl-butyl)phenyl]-1H-pyrazole-4-carboxamide | (4.1.4) tau-fluvalinate |
| (1-8) 5-fluoro-1,3-dimethyl-N-[2-(1,3,3-trimethyl-butyl)phenyl]-1H-pyrazole-4-carboxamide | (4.2.1) indoxacarb |
| (1-8) 5-fluoro-1,3-dimethyl-N-[2-(1,3,3-trimethyl-butyl)phenyl]-1H-pyrazole-4-carboxamide | (5.1.1) spinosad |
| (1-8) 5-fluoro-1,3-dimethyl-N-[2-(1,3,3-trimethyl-butyl)phenyl]-1H-pyrazole-4-carboxamide | (6.1.1) endosulfan |
| (1-8) 5-fluoro-1,3-dimethyl-N-[2-(1,3,3-trimethyl-butyl)phenyl]-1H-pyrazole-4-carboxamide | (6.2.1) fipronil |
| (1-8) 5-fluoro-1,3-dimethyl-N-[2-(1,3,3-trimethyl-butyl)phenyl]-1H-pyrazole-4-carboxamide | (6.2.2) ethiprole |
| (1-8) 5-fluoro-1,3-dimethyl-N-[2-(1,3,3-trimethyl-butyl)pheny]-1H-pyrazole-4-carboxamide | (7.1.1) emamectin-benzoate |
| (1-8) 5-fluoro-1,3-dimethyl-N-[2-(1,3,3-trimethyl-butyl)phenyl]-1H-pyrazole-4-carboxamide | (8.1.1) pyriproxifen |
| (1-8) 5-fluoro-1,3-dimethyl-N-[2-(1,3,3-trimethyl-butyl)phenyl]-1H-pyrazole-4-carboxamide | (9.1.1) methoxyfenozide |
| (1-8) 5-fluoro-1,3-dimethyl-N-[2-(1,3,3-trimethyl-butyl)phenyl]-1H-pyrazole-4-carboxamide | (10.1.1) triflumuron |
| (1-8) 5-fluoro-1,3-dimethyl-N-[2-(1,3,3-trimethyl-butyl)phenyl]-1H-pyrazole-4-carboxamide | (10.1.2) flufenoxuron |
| (1-8) 5-fluoro-1,3-dimethyl-N-[2-(1,3,3-trimethyl-butyl)phenyl]-1H-pyrazole-4-carboxamide | (13.1.1) tebufenpyrad |
| (1-8) 5-fluoro-1,3-dimethyl-N-[2-(1,3,3-trimethyl-butyl)phenyl]-1H-pyrazole-4-carboxamide | (13.2.1) hydramethylone |
| (1-8) 5-fluoro-1,3-dimethyl-N-[2-(1,3,3-trimethyl-butyl)phenyl]-1H-pyrazole-4-carboxamide | (17.1.1) spirodiclofen |
| (1-8) 5-fluoro-1,3-dimethyl-N-[2-(1,3,3-trimethyl-butyl)phenyl]-1H-pyrazole-4-carboxamide | (17.1.2) spiromesifen |
| (1-8) 5-fluoro-1,3-dimethyl-N-[2-(1,3,3-trimethyl-butyl)phenyl]-1H-pyrazole-4-carboxamide | (17.2.1) 3-(2,5-dimethylphenyl)-8-methoxy-2-oxo-1-azaspiro[4.5]dec-3-en-4-yl ethyl carbonate |
| (1-8) 5-fluoro-1,3-dimethyl-N-[2-(1,3,3-trimethyl-butyl)phenyl]-1H-pyrazole-4-carboxamide | (18.1.1) flonicamid |
| (1-8) 5-fluoro-1,3-dimethyl-N-[2-(1,3,3-trimethyl-butyl)phenyl]-1H-pyrazole-4-carboxamide | (21.1.1) flubendiamide |
| (1-2) N-[2-(1,3-dimethylbutyl)phenyl]-5-fluoro-1,3-dimethyl-1H-pyrazole-4-carboxamide | (2.1.1) clothianidin |
| (1-2) N-[2-(1,3-dimethylbutyl)phenyl]-5-fluoro-1,3-dimethyl-1H-pyrazole-4-carboxamide | (2.1.2) imidacloprid |
| (1-2) N-[2-(1,3-dimethylbutyl)phenyl]-5-fluoro-1,3-dimethyl-1H-pyrazole-4-carboxamide | (2.1.3) thiacloprid |
| (1-2) N-[2-(1,3-dimethylbutyl)phenyl]-5-fluoro-1,3-dimethyl-1H-pyrazole-4-carboxamide | (2.1.4) thiamethoxam |
| (1-2) N-[2-(1,3-dimethylbutyl)phenyl]-5-fluoro-1,3-dimethyl-1H-pyrazole-4-carboxamide | (3.1.1) methiocarb |
| (1-2) N-[2-(1,3-dimethylbutyl)phenyl]-5-fluoro-1,3-dimethyl-1H-pyrazole-4-carboxamide | (3.1.2) thiodoicarb |
| (1-2) N-[2-(1,3-dimethylbutyl)phenyl]-5-fluoro-1,3-dimethyl-1H-pyrazole-4-carboxamide | (3.1.3) ethiofencarb |
| (1-2) N-[2-(1,3-dimethylbutyl)phenyl]-5-fluoro-1,3-dimethyl-1H-pyrazole-4-carboxamide | (3.2.1) azinphos-methyl |
| (1-2) N-[2-(1,3-dimethylbutyl)phenyl]-5-fluoro-1,3-dimethyl-1H-pyrazole-4-carboxamide | (3.2.2) azinphos-ethyl |
| (1-2) N-[2-(1,3-dimethylbutyl)phenyl]-5-fluoro-1,3-dimethyl-1H-pyrazole-4-carboxamide | (4.1.1) beta-cyfluthrin |
| (1-2) N-[2-(1,3-dimethylbutyl)phenyl]-5-fluoro-1,3-dimethyl-1H-pyrazole-4-carboxamide | (4.1.2) cyfluthrin |
| (1-2) N-[2-(1,3-dimethylbutyl)phenyl]-5-fluoro-1,3-dimethyl-1H-pyrazole-4-carboxamide | (4.1.3) deltamethrin |
| (1-2) N-[2-(1,3-dimethylbutyl)phenyl]-5-fluoro-1,3-dimethyl-1H-pyrazole-4-carboxamide | (4.1.4) tau-fluvalinate |

TABLE 1-continued

| Active compound of group (1) | Active compound of groups (2) to (24) |
|---|---|
| (1-2) N-[2-(1,3-dimethylbutyl)phenyl]-5-fluoro-1,3-dimethyl-1H-pyrazole-4-carboxamide | (4.2.1) indoxacarb |
| (1-2) N-[2-(1,3-dimethylbutyl)phenyl]-5-fluoro-1,3-dimethyl-1H-pyrazole-4-carboxamide | (5.1.1) spinosad |
| (1-2) N-[2-(1,3-dimethylbutyl)phenyl]-5-fluoro-1,3-dimethyl-1H-pyrazole-4-carboxamide | (6.1.1) endosulfan |
| (1-2) N-[2-(1,3-dimethylbutyl)phenyl]-5-fluoro-1,3-dimethyl-1H-pyrazole-4-carboxamide | (6.2.1) fipronil |
| (1-2) N-[2-(1,3-dimethylbutyl)phenyl]-5-fluoro-1,3-dimethyl-1H-pyrazole-4-carboxamide | (6.2.2) ethiprole |
| (1-2) N-[2-(1,3-dimethylbutyl)phenyl]-5-fluoro-1,3-dimethyl-1H-pyrazole-4-carboxamide | (7.1.1) emamectin-benzoate |
| (1-2) N-[2-(1,3-dimethylbutyl)phenyl]-5-fluoro-1,3-dimethyl-1H-pyrazole-4-carboxamide | (8.1.1) pyriproxifen |
| (1-2) N-[2-(1,3-dimethylbutyl)phenyl]-5-fluoro-1,3-dimethyl-1H-pyrazole-4-carboxamide | (9.1.1) methoxyfenozide |
| (1-2) N-[2-(1,3-dimethylbutyl)phenyl]-5-fluoro-1,3-dimethyl-1H-pyrazole-4-carboxamide | (10.1.1) triflumuron |
| (1-2) N-[2-(1,3-dimethylbutyl)phenyl]-5-fluoro-1,3-dimethyl-1H-pyrazole-4-carboxamide | (10.1.2) flufenoxuron |
| (1-2) N-[2-(1,3-dimethylbutyl)phenyl]-5-fluoro-1,3-dimethyl-1H-pyrazole-4-carboxamide | (13.1.1) tebufenpyrad |
| (1-2) N-[2-(1,3-dimethylbutyl)phenyl]-5-fluoro-1,3-dimethyl-1H-pyrazole-4-carboxamide | (13.2.1) hydramethylone |
| (1-2) N-[2-(1,3-dimethylbutyl)phenyl]-5-fluoro-1,3-dimethyl-1H-pyrazole-4-carboxamide | (17.1.1) spirodiclofen |
| (1-2) N-[2-(1,3-dimethylbutyl)phenyl]-5-fluoro-1,3-dimethyl-1H-pyrazole-4-carboxamide | (17.1.2) spiromesifen |
| (1-2) N-[2-(1,3-dimethylbutyl)phenyl]-5-fluoro-1,3-dimethyl-1H-pyrazole-4-carboxamide | (17.2.1) 3-(2,5-dimethylphenyl)-8-methoxy-2-oxo-1-azaspiro[4.5]dec-3-en-4-yl ethyl carbonate |
| (1-2) N-[2-(1,3-dimethylbutyl)phenyl]-5-fluoro-1,3-dimethyl-1H-pyrazole-4-carboxamide | (18.1.1) flonicamid |
| (1-2) N-[2-(1,3-dimethylbutyl)phenyl]-5-fluoro-1,3-dimethyl-1H-pyrazole-4-carboxamide | (21.1.1) flubendiamide |
| (1-15) N-[2-(1,3-dimethylbutyl)phenyl]-2-(trifluoromethyl)benzamide | (2.1.1) clothianidin |
| (1-15) N-[2-(1,3-dimethylbutyl)phenyl]-2-(trifluoromethyl)benzamide | (2.1.2) imidacloprid |
| (1-15) N-[2-(1,3-dimethylbutyl)phenyl]-2-(trifluoromethyl)benzamide | (2.1.3) thiacloprid |
| (1-15) N-[2-(1,3-dimethylbutyl)phenyl]-2-(trifluoromethyl)benzamide | (2.1.4) thiamethoxam |
| (1-15) N-[2-(1,3-dimethylbutyl)phenyl]-2-(trifluoromethyl)benzamide | (3.1.1) methiocarb |
| (1-15) N-[2-(1,3-dimethylbutyl)phenyl]-2-(trifluoromethyl)benzamide | (3.1.2) thiodoicarb |
| (1-15) N-[2-(1,3-dimethylbutyl)phenyl]-2-(trifluoromethyl)benzamide | (3.1.3) ethiofencarb |
| (1-15) N-[2-(1,3-dimethylbutyl)phenyl]-2-(trifluoromethyl)benzamide | (3.2.1) azinphos-methyl |
| (1-15) N-[2-(1,3-dimethylbutyl)phenyl]-2-(trifluoromethyl)benzamide | (3.2.2) azinphos-ethyl |
| (1-15) N-[2-(1,3-dimethylbutyl)phenyl]-2-(trifluoromethyl)benzamide | (4.1.1) beta-cyfluthrin |
| (1-15) N-[2-(1,3-dimethylbutyl)phenyl]-2-(trifluoromethyl)benzamide | (4.1.2) cyfluthrin |
| (1-15) N-[2-(1,3-dimethylbutyl)phenyl]-2-(trifluoromethyl)benzamide | (4.1.3) deltamethrin |
| (1-15) N-[2-(1,3-dimethylbutyl)phenyl]-2-(trifluoromethyl)benzamide | (4.1.4) tau-fluvalinate |
| (1-15) N-[2-(1,3-dimethylbutyl)phenyl]-2-(trifluoromethyl)benzamide | (4.2.1) indoxacarb |
| (1-15) N-[2-(1,3-dimethylbutyl)phenyl]-2-(trifluoromethyl)benzamide | (5.1.1) spinosad |
| (1-15) N-[2-(1,3-dimethylbutyl)phenyl]-2-(trifluoromethyl)benzamide | (6.1.1) endosulfan |
| (1-15) N-[2-(1,3-dimethylbutyl)phenyl]-2-(trifluoromethyl)benzamide | (6.2.1) fipronil |
| (1-15) N-[2-(1,3-dimethylbutyl)phenyl]-2-(trifluoromethyl)benzamide | (6.2.2) ethiprole |
| (1-15) N-[2-(1,3-dimethylbutyl)phenyl]-2-(trifluoromethyl)benzamide | (7.1.1) emamectin-benzoate |
| (1-15) N-[2-(1,3-dimethylbutyl)phenyl]-2-(trifluoromethyl)benzamide | (8.1.1) pyriproxifen |
| (1-15) N-[2-(1,3-dimethylbutyl)phenyl]-2-(trifluoromethyl)benzamide | (9.1.1) methoxyfenozide |
| (1-15) N-[2-(1,3-dimethylbutyl)phenyl]-2-(trifluoromethyl)benzamide | (10.1.1) triflumuron |

TABLE 1-continued

| Active compound of group (1) | Active compound of groups (2) to (24) |
|---|---|
| (1-15) N-[2-(1,3-dimethylbulyl)phenyl]-2-(trifluoromethyl)benzamide | (10.1.2) flufenoxuron |
| (1-15) N-[2-(1,3-dimethylbutyl)phenyl]-2-(trifluoromethyl)benzamide | (13.1.1) tebufenpyrad |
| (1-15) N-[2-(1,3-dimethylbutyl)phenyl]-2-(trifluoromethyl)benzamide | (13.2.1) hydramethylone |
| (1-15) N-[2-(1,3-dimethylbutyl)phenyl]-2-(tnfluoromethyl)benzamide | (17.1.1) spirodiclofen |
| (1-15) N-[2-(1,3-dimethylbutyl)phenyl]-2-(trifluoromethyl)benzamide | (17.1.2) spiromesifen |
| (1-15) N-[2-(1,3-dimethylbutyl)phenyl]-2-(trifluoromethyl)benzamide | (17.2.1) 3-(2,5-dimethylphenyl)-8-methoxy-2-oxo-1-azaspiro[4.5]dec-3-en-4-yl ethyl carbonate |
| (1-15) N-[2-(1,3-dimethylbutyl)phenyl]-2-(trifluoromethyl)benzamide | (18.1.1) flonicamid |
| (1-15) N-[2-(1,3-dimethylbutyl)phenyl]-2-(trifluoromethyl)benzamide | (21.1.1) flubendiamide |
| (1-13) N-[2-(1,3-dimethylbutyl)phenyl]-2-iodobenzamide | (2.1.1) clothianidin |
| (1-13) N-[2-(1,3-dimethylbutyl)phenyl]-2-iodobenzamide | (2.1.2) imidacloprid |
| (1-13) N-[2-(1,3-dimethylbutyl)phenyl]-2-iodobenzamide | (2.1.3) thiacloprid |
| (1-13) N-[2-(1,3-dimethylbutyl)phenyl]-2-iodobenzamide | (2.1.4) thiamethoxam |
| (1-13) N-[2-(1,3-dimethylbutyl)phenyl]-2-iodobenzamide | (3.1.1) methiocarb |
| (1-13) N-[2-(1,3-dimethylbutyl)phenyl]-2-iodobenzamide | (3.1.2) thiodoicarb |
| (1-13) N-[2-(1,3-dimethylbutyl)phenyl]-2-iodobenzamide | (3.1.3) ethiofencarb |
| (1-13) N-[2-(1,3-dimethylbutyl)phenyl]-2-iodobenzamide | (3.2.1) azinphos-methyl |
| (1-13) N-[2-(1,3-dimethylbutyl)phenyl]-2-iodobenzamide | (3.2.2) azinphos-ethyl |
| (1-13) N-[2-(1,3-dimethylbutyl)phenyl]-2-iodobenzamide | (4.1.1) beta-cyfluthrin |
| (1-13) N-[2-(1,3-dimethylbutyl)phenyl]-2-iodobenzamide | (4.1.2) cyfluthrin |
| (1-13) N-[2-(1,3-dimethylbutyl)phenyl]-2-iodobenzamide | (4.1.3) deltamethrin |
| (1-13) N-[2-(1,3-dimethylbutyl)phenyl]-2-iodobenzamide | (4.1.4) tau-fluvalinate |
| (1-13) N-[2-(1,3-dimethylbutyl)phenyl]-2-iodobenzamide | (4.2.1) indoxacarb |
| (1-13) N-[2-(1,3-dimethylbutyl)phenyl]-2-iodobenzamide | (5.1.1) spinosad |
| (1-13) N-[2-(1,3-dimethylbutyl)phenyl]-2-iodobenzamide | (6.1.1) endosulfan |
| (1-13) N-[2-(1,3-dimethylbutyl)phenyl]-2-iodobenzamide | (6.2.1) fipronil |
| (1-13) N-[2-(1,3-dimethylbutyl)phenyl]-2-iodobenzamide | (6.2.2) ethiprole |
| (1-13) N-[2-(1,3-dimethylbutyl)phenyl]-2-iodobenzamide | (7.1.1) emamectin-benzoate |
| (1-13) N-[2-(1,3-dimethylbutyl)phenyl]-2-iodobenzamide | (8.1.1) pyriproxyfen |
| (1-13) N-[2-(1,3-dimethylbutyl)phenyl]-2-iodobenzamide | (9.1.1) methoxyfenozide |
| (1-13) N-[2-(1,3-dimethylbutyl)phenyl]-2-iodobenzamide | (10.1.1) triflumuron |
| (1-13) N-[2-(1,3-dimethylbutyl)phenyl]-2-iodobenzamide | (10.1.2) flufenoxuron |
| (1-13) N-[2-(1,3-dimethylbutyl)phenyl]-2-iodobenzamide | (13.1.1) tebufenpyrad |
| (1-13) N-[2-(1,3-dimethylbutyl)phenyl]-2-iodobenzamide | (13.2.1) hydramethylone |
| (1-13) N-[2-(1,3-dimethylbutyl)phenyl]-2-iodobenzamide | (17.1.1) spirodiclofen |
| (1-13) N-[2-(1,3-dimethylbutyl)phenyl]-2-iodobenzamide | (17.1.2) spiromesifen |
| (1-13) N-[2-(1,3-dimethylbutyl)phenyl]-2-iodobenzamide | (17.2.1) 3-(2,5-dimethylphenyl)-8-methoxy-2-oxo-1-azaspiro[4.5]dec-3-en-4-yl ethyl carbonate |
| (1-13) N-[2-(1,3-dimethylbutyl)phenyl]-2-iodobenzamide | (18.1.1) flonicamid |
| (1-13) N-[2-(1,3-dimethylbutyl)phenyl]-2-iodobenzamide | (21.1.1) flubendiamide |

In addition, the active compound combinations may also comprise further fungicially, acaricidally or insecticidally effective added components.

If the active compounds in the active compound combinations according to the invention are present in certain weight ratios, the synergistic effect is particularly pronounced. However, the weight ratios of the active compounds in the active compound combinations can be varied within a relatively wide range. In general, the combinations according to the invention comprise active compounds of the formula (I) and the mixing partner in the preferred mixing ratios given in the table below, where the mixing ratios are based on weight ratios.

The ratio is to be understood as meaning active compound of the formula (I) (group 1):mixing partner.

TABLE 2

Mixing ratios

| Mixing partner (group) | Preferred mixing ratio | Particularly preferred mixing ratio |
|---|---|---|
| (2.1) chloronicotinyls/neonicotinoids | 500:1 to 1:50 | 125:1 to 1:25 |
| (2.2) nicotine, bensultap, cartap | 500:1 to 1:50 | 125:1 to 1:25 |
| (3.1) carbamates | 500:1 to 1:1000 | 125:1 to 1:500 |
| (3.2) organophosphates | 500:1 to 1:50 | 125:1 to 1:25 |
| (4.1) pyrethroids | 500:1 to 1:50 | 125:1 to 1:25 |
| (4.2) oxadiazines | 500:1 to 1:50 | 125:1 to 1:25 |
| (5.1) spinosyns | 500:1 to 1:50 | 125:1 to 1:25 |
| (6.1) cyclodiene organochlorines | 500:1 to 1:50 | 125:1 to 1:25 |
| (6.2) fiproles | 500:1 to 1:200 | 125:1 to 1:50 |
| (7.1) mectins | 500:1 to 1:50 | 125:1 to 1:25 |
| (8) juvenile hormone mimetics | 500:1 to 1:50 | 125:1 to 1:25 |
| (9.1) diacylhydrazines | 500:1 to 1:50 | 125:1 to 1:25 |
| (10.1) benzoylureas | 500:1 to 1:50 | 125:1 to 1:25 |
| (10.2) buprofezin | 500:1 to 1:50 | 125:1 to 1:25 |
| (10.3) cyromazine | 500:1 to 1:50 | 125:1 to 1:25 |
| (11.1) diafenthiuron | 500:1 to 1:50 | 125:1 to 1:25 |
| (11.2) organotins | 500:1 to 1:50 | 125:1 to 1:25 |
| (12.1) pyrroles | 500:1 to 1:50 | 125:1 to 1:25 |
| (12.2) dinitrophenols | 500:1 to 1:50 | 125:1 to 1:25 |
| (13.1) METIs | 500:1 to 1:50 | 125:1 to 1:25 |
| (13.2) hydramethylnone | 500:1 to 1:50 | 125:1 to 1:25 |
| (13.3) dicofol | 500:1 to 1:50 | 125:1 to 1:25 |
| (14) rotenone | 500:1 to 1:50 | 125:1 to 1:25 |
| (15.1) acequinocyl, fluacrypyrim | 500:1 to 1:50 | 125:1 to 1:25 |
| (16.1) *Bacillus thuringiensis* strains | 500:1 to 1:50 | 125:1 to 1:25 |
| (17.1) tetronic acids | 500:1 to 1:50 | 125:1 to 1:25 |
| (17.2) tetramic acids | 500:1 to 1:50 | 125:1 to 1:25 |
| (18) flonicamid | 500:1 to 1:50 | 125:1 to 1:25 |
| (19) amitraz | 500:1 to 1:50 | 125:1 to 1:25 |
| (20) propargite | 500:1 to 1:50 | 125:1 to 1:25 |
| (21) phthalamides | 500:1 to 1:50 | 125:1 to 1:25 |
| (22) nereistoxin analogues | 500:1 to 1:50 | 125:1 to 1:25 |
| (23) biologics, hormones, pheromones | 500:1 to 1:50 | 125:1 to 1:25 |
| (24.1) fumigants | 500:1 to 1:50 | 125:1 to 1:25 |
| (24.2) selective feeding inhibitors | 500:1 to 1:50 | 125:1 to 1:25 |
| (24.3) mite growth inhibitors | 500:1 to 1:50 | 125:1 to 1:25 |
| (24.4) | 500:1 to 1:50 | 125:1 to 1:25 |

The active compound combinations according to the invention have strong microbicidal action and can be used for controlling unwanted microorganisms, such as fungi and bacteria, in crop protection and in the protection of materials.

In crop protection, fungicides can be used for controlling *Plasmodiophoromycetes, Oomycetes, Chytridiomycetes, Zygomycetes, Ascomycetes, Basidiomycetes* and *Deuteromycetes*.

In crop protection, bactericides can be used for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

diseases caused by powdery mildew pathogens, such as, for example,

*Blumeria* species, such as, for example, *Blumeria graminis*;
*Podosphaera* species, such as, for example, *Podosphaera leucotricha*;
*Sphaerotheca* species, such as, for example, *Sphaerotheca fuliginea*;
*Uncinula* species, such as, for example, *Uncinula necator*;

diseases caused by rust disease pathogens, such as, for example,

*Gymnosporangium* species, such as, for example, *Gymnosporangium sabinae*
*Hemileia* species, such as, for example, *Hemileia vastatrix*;
*Phakopsora* species, such as, for example, *Phakopsora pachyrhizi* and *Phakopsora meibomiae*;
*Puccinia* species, such as, for example, *Puccinia recondita*;
*Uromyces* species, such as, for example, *Uromyces appendiculatus*;

diseases caused by pathogens from the group of the Oomycetes, such as, for example,

*Bremia* species, such as, for example, *Bremia lactucae*;
*Peronospora* species, such as, for example, *Peronospora pisi* or *P. brassicae*;
*Phytophthora* species, such as, for example *Phytophthora infestans*;
*Plasmopara* species, such as, for example, *Plasmopara viticola*;
*Pseudoperonospora* species, such as, for example, *Pseudoperonospora humuli* or
*Pseudoperonospora cubensis*;
*Pythium* species, such as, for example, *Pythium ultimum*;

leaf blotch diseases and leaf wilt diseases caused, for example, by

*Alternaria* species, such as, for example, *Alternaria solani*;
*Cercospora* species, such as, for example, *Cercospora beticola*;
*Cladiosporum* species, such as, for example, *Cladiosporium cucumerinum*;
*Cochliobolus* species, such as, for example, *Cochliobolus sativus*
(conidia form: *Drechslera*, Syn: *Helminthosporium*);
*Colletotrichum* species, such as, for example, *Colletotrichum lindemuthanium*;
*Cycloconium* species, such as, for example, *Cycloconium oleaginum*;
*Diaporthe* species, such as, for example, *Diaporthe citri*;
*Elsinoe* species, such as, for example, *Elsinoe fawcettii*;
*Gloeosporium* species, such as, for example, *Gloeosporium laeticolor*;
*Glomerella* species, such as, for example, *Glomerella cingulata*;
*Guignardia* species, such as, for example, *Guignardia bidwelli*;
*Leptosphaeria* species, such as, for example, *Leptosphaeria maculans*;
*Magnaporthe* species, such as, for example, *Magnaporthe grisea*;
*Mycosphaerella* species, such as, for example, *Mycosphaerelle graminicola*;
*Phaeosphaeria* species, such as, for example, *Phaeosphaeria nodorum*;
*Pyrenophora* species, such as, for example, *Pyrenophora teres*;

*Ramularia* species, such as, for example, *Ramularia collocygni;*
*Rhynchosporium* species, such as, for example, *Rhynchosporium secalis;*
*Septoria* species, such as, for example, *Septoria apii;*
*Typhula* species, such as, for example, *Typhula incarnata;*
*Venturia* species, such as, for example, *Venturia inacqualis;*
root and stem diseases caused, for example, by
*Corticium* species, such as, for example, *Corticium graminearum;*
*Fusarium* species, such as, for example, *Fusarium oxysporum;*
*Gaeumannomyces* species, such as, for example, *Gaeumannomyces graminis;*
*Rhizoctonia* species, such as, for example *Rhizoctonia solani;*
*Tapesia* species, such as, for example, *Tapesia acuformis;*
*Thielaviopsis* species, such as, for example, *Thielaviopsis basicola;*
ear and panicle diseases (including maize crops) caused, for example, by
*Alternaria* species, such as, for example, *Alternaria* spp.;
*Aspergillus* species, such as, for example, *Aspergillus flavus;*
*Cladosporium* species, such as, for example, *Cladosporium* spp.;
*Claviceps* species, such as, for example, *Claviceps purpurea;*
*Fusarium* species, such as, for example, *Fusarium culmorum;*
*Gibberella* species, such as, for example, *Gibberella zeae;*
*Monographella* species, such as, for example, *Monographella nivalis;*
diseases caused by smut fungi, such as, for example,
*Sphacelotheca* species, such as, for example, *Sphacelotheca reiliana;*
*Tilletia* species, such as, for example, *Tilletia caries;*
*Urocystis* species, such as, for example, *Urocystis occulta;*
*Ustilago* species, such as, for example, *Ustilago nuda;*
fruit rot caused, for example, by
*Aspergillus* species, such as, for example, *Aspergillus flavus;*
*Botrytis* species, such as, for example, *Botrytis cinerea;*
*Penicillium* species, such as, for example, *Penicillium expansum;*
*Sclerotinia* species, such as, for example, *Sclerotinia sclerotiorum;*
*Verticilium* species, such as, for example, *Verticilium alboatrum;*
seed- and soil-borne rot and wilt diseases, and also diseases of seedlings, caused, for example, by
*Fusarium* species, such as, for example, *Fusarium culmorum;*
*Phytophthora* species, such as, for example, *Phytophthora cactorum;*
*Pythium* species, such as, for example, *Pythium ultimum;*
*Rhizoctonia* species, such as, for example, *Rhizoctonia solani;*
*Sclerotium* species, such as, for example, *Sclerotium rolfsii;*
cancerous diseases, galls and witches' broom caused, for example, by
*Nectria* species, such as, for example, *Nectria galligena;*
wilt diseases caused, for example, by
*Monilinia* species, such as, for example, *Monilinia laxa;*
deformations of leaves, flowers and fruits caused, for example, by
*Taphrina* species, such as, for example, *Taphrina deformans;*
degenerative diseases of woody plants caused, for example, by
*Esca* species, such as, for example, *Phaemoniella clamydospora;*
diseases of flowers and seeds caused, for example, by
*Botrytis* species, such as, for example, *Botrytis cinerea;*
diseases of plant tubers caused, for example, by
*Rhizoctonia* species, such as, for example, *Rhizoctonia solani;*
*Helminthosporium* species, such as, for example *Helminthosporium solani;*
diseases cause by bacterial pathogens, such as, for example,
*Xanthomonas* species, such as, for example *Xanthomonas campestris* pv. *oryzae;*
*Pseudomonas* species, such as, for example, *Pseudomonas syringae* pv. *lachrymans;*
*Erwinia* species, such as, for example, *Erwinia amylovora.*

With preference, it is possible to control the following diseases of soya beans:

fungal diseases on leaves, stems, pods and seeds, caused, for example, by
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera* trispora (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

Fungal diseases on roots and the stem base, caused, for example, by
black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotioruim*), sclerotinia southern blight (*Sclerotinia rolfsii*), thielaviopsis root rot (*Thielaviopsis basicola*).

The fact that the active compound combinations are well tolerated by plants at the concentrations required for controlling plant diseases permits a treatment of entire plants (aboveground parts of plants and roots), of propagation stock and seed, and of the soil. The active compound combinations according to the invention can be used for foliar application or else as seed dressings.

The fact that the active compounds which can be used are well tolerated by plants at the concentrations required for controlling plant diseases permits a treatment of the seed. Accordingly, the active compounds according to the invention can be used as seed dressings.

A large part of the damage to crop plants which is caused by phytopathogenic fungi occurs as early as when the seed is attacked during storage and after the seed is introduced into the soil, as well as during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fingi by treating the seeds of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants or where additional application is at least reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the composition according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that, by virtue of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of seed of cereals (such as wheat, barley, rye and oats), maize and rice is of particular importance.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations according to the invention also have a potent strengthening effect in plants. They are therefore suitable for mobilizing the plants' defences against attack by undesired microorganisms.

Plant-strengthening (resistance-inducing) substances are understood as meaning, in the present context, those substances which are capable of stimulating the defence system of plants in such a way that, when subsequently inoculated with undesired microorganisms, the treated plants display a substantial degree of resistance to these microorganisms.

In the present case, undesired microorganisms are understood as meaning phytopathogenic fungi, bacteria and viruses. Thus, the compounds according to the invention can be employed for protecting plants against attack by the abovementioned pathogens within a certain period of time after the treatment. The period of time within which their protection is effected is generally extended from 1 to 10 days, preferably 1 to 7 days, after the plants have been treated with the active compounds.

The fact that the active compound combinations, at the concentrations required for the controlling of plant diseases, are well tolerated by plants permits the treatment of aerial plant parts, of vegetative propagation material and seed, and of the soil.

In this context, the active compound combinations according to the invention can be employed particularly successfully for controlling cereal diseases such as, for example, against *Puccinia* species and diseases in viticulture, fruit production and vegetable production such as, for example against *Botrytis, Venturia* or *Alternaria* species.

The active compound combinations according to the invention are also suitable for increasing the yield of crops. In addition, they show reduced toxicity and are well tolerated by plants.

If appropriate, the active compound combinations according to the invention can also be used in certain concentrations and application rates as herbicides, for influencing plant growth and for controlling animal pests. If appropriate, they can also be employed as intermediates and precursors for the synthesis of further active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compound combinations is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the active compound combinations according to the invention can be employed for protecting industrial materials against attack and destruction by undesired microorganisms.

In the present context, industrial materials are understood as meaning non-live materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (*Basidiomycetes*) and against slime organisms and algae.

Examples which may be mentioned are microorganisms of the following genera:
*Alternaria* such as *Alternaria tenuis*,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicillium* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viride*,
*Escherichia* such as *Escherichia coli*,
*Pseudomonas* such as *Pseudomonas aeruginosa*,
*Staphylococcus* such as *Staphylococcus aureus*.

In addition, the active compound combinations according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi is no restriction whatsoever of the mycotic spectrum which can be controlled and is provided by illustration only.

The active compound combinations can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plant can also be treated.

When employing the active compound combinations according to the invention as fungicides, the application rates can be varied within a substantial range, depending on the type of application. In the treatment of plant parts, the application rates of active compound are generally between 0.1 and 10000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10000 g/ha, preferably between 1 and 5000 g/ha.

According to the invention, the plants listed can be treated particularly advantageously with the active compound mixtures according to the invention. The preferred ranges indicated above for the active compounds and mixtures also apply to the treatment of these plants. Particular emphasis is given to the treatment of plants with compounds or mixtures specifically indicated in the present text.

The active compound combinations according to the invention are also suitable for controlling animal pests, preferably anthropods and nematodes, in particular nematodes and insects, which are encountered in agriculture, in animal health, in forestry, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus, Gryllotalpa* spp., *Locusta migratoria migratorioides, Melanoplus* spp. and *Schistocerca gregaria*.

From the order of the Blattaria, for example, *Blatta orientalis, Periplaneta americana, Leucophaea maderae, Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella occidentalis*.

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

Depending on the respective physical and/or chemical properties, the active compound combinations can be converted to the customary formulations, such as solutions, emulsions, wettable powders, suspensions, powders, foams, dusts, pastes, soluble powders, granules, aerosols, suspoemulsion concentrates, natural and synthetic materials impregnated with active compound and microencapsulations in polymeric substances and in coating materials for seed, and also ULV cold and warm fogging formulations.

These formulations are produced in a known manner, for example by mixing the active compounds with extenders, that is liquid solvents, and/or solid carriers, optionally with the use of surfactants, that is emulsifiers and/or dispersants, and/or foam-formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable: for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marling devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as *Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate*

*monachus, Bostrychus capucins, Heterobostrychus brunneus, Sinoxylon* spec., *Dinoderus minutus*.

Dermapterans such as *Sirex juvencus, Urocerus gigas, Urocerus gigas* taignus, *Urocerus augur*. Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*.

Bristle-tails such as *Lepisma saccharina*.

Industrial materials in the present context are understood as meaning non-living materials such as, preferably, polymers, glues, sizes, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example: construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flashpoint of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flashpoint of above 30° C., preferably above 45° C., can be replaced in part by organochemical solvents of high or medium volatility, with the proviso that the solvent mixture also has an evaporation number of above 35 and a flashpoint of above 30° C., preferably above 45° C., and that the mixture is soluble or emulsifiable in this solvent mixture.

In a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl)adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can equally be employed for protecting objects which come into contact with saltwater or brackish water, in particular hulls, screens, nets, buildings, quaysides and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., in particular fouling by sessile Entomostraka groups, which come under the generic term Cirripedia (cirriped crustaceans), is of particular importance.

Surprisingly, it has now been found that the active compound combinations according to the invention have an outstanding antifouling action.

Use of the active compound combinations according to the invention allows the use of heavy metals such as, for example, in bis(trialkyltin) sulphides, tri-n-butyltin laurate, tri-n-butyltin chloride, copper(I) oxide, triethyltin chloride, tri-n-butyl (2-phenyl-4-chlorophenoxy)tin, tributyltin oxide, molybdenum disulphide, antimony oxide, polymeric butyl titanate, phenyl (bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferable suitable components in combinations for the antifouling compositions according to the invention are:
algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as benzo[b]thiophenecarboxylic acid cyclohexylamide S,S-dioxide, dichiofluanid, fluorfolpet, 3-iodo-2-propynyl butylcarbamate, tolylfluanid and azoles such as azaconazole, cyproconazole, epoxyconazole, hexaconazole, metconazole, propiconazole and tebuconazole;
molluscicides such as fentin acetate, metaldehyde, methiocarb, niclosamid, thiodicarb and trimethacarb; or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium salts, copper salts, sodium salts and zinc salts of 2-pyridinethiol 1-oxide, pyridine-triphenylborane, tetrabutyl-distannoxane, 2,3,5,6-tetrachloro-4-(methylsulphonyl)pyridine, 2,4,5,6-tetrachloroisophthalonitrile, tetramethylthiuram disulphide and 2,4,6-trichlorophenylmaleimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumen, asphalt and epoxy compounds, small amounts of chlorine rubber, chlorinated polypropylene and vinyl resins.

If appropriate, paints also comprise inorganic pigments, organic pigments or colorants which are preferably insoluble in seawater. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus* capitis, *Pediculus humanus* corporis, *Phthirus pubis.*

From the order of the Heteroptera, for example, *Cimex hemipterus, Cimex lectularius, Rhodnius prolixus, Triatoma infestans.*

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, more developed root system, better resistance of the plant species or plant cultivar, increased shoot growth, increased plant vitality, increased tolerance to high or low temperatures, increased tolerance to drought or to water or soil salt content, increased flowering performance, easier harvesting, accelerated maturation, higher harvest yields, larger fruit, larger plants, greener leaves, earlier flowers, better quality and/or a higher nutritional value of the harvested products, higher concentration of sugar in the fruit, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects, by toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

According to the invention, the plants listed can be treated particularly advantageously with the active compound mixtures according to the invention. The abovementioned preferred ranges for the mixtures also apply for the treatment of these plants. The treatment of plants with the mixtures especially listed in the present text are particularly emphasized.

The good action of the insecticidal, acaricidal and fungicidal active compound combinations according to the invention is demonstrated by the examples below. While the individual active compounds show weaknesses in their fungicidal action, the combinations show an action which exceeds a simple sum of actions.

A synergistic effect in insecticides, acaricides and fungicides is always present when the insecticidal or fungicidal action of the active compound combinations exceeds the total of the action of the active compounds when applied individually.

The expected insecticidal, acaricidal and fungicidal action for a given combination of two active compounds can be calculated as follows, according to S. R. Colby ("Calculating Synergistic and Antagonistic Responses of Herbicide Combinations", Weeds 1967, 15, 20-22):

If

X is the kill rate expressed in % of the untreated control when employing active compound A at an application rate of m g/ha or at a concentration of m ppm, Y is the kill rate expressed in % of the untreated control when employing active compound B at an application rate of n g/ha or at a concentration of n ppm and E is the kill rate expressed in % of the untreated control when employing active compounds A and B at application rates of m and n g/ha or at a concentration of m and n ppm, then $$E = X + Y \cdot \frac{X \times Y}{100}$$

If the actual insecticidal, acaricidal and fungicidal kill rate exceeds the calculated value, the kill rate of the combination is superadditive, i.e. a synergistic effect is present. In this case, the actually observed kill rate must exceed the value calculated using the above formula for the expected kill rate (E).

EXAMPLES

Example A

*Myzus persicae*-Test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed. The determined kill rates are calculated using Colby's formula (see sheet 1).

In this test, for example, the following active compound combination according to the present application has a synergistically enhanced activity compared to the active compounds applied on their own:

TABLE A

Plant-damaging insects: *Myzus persicae* - Test

| Active compounds | Active compound concentration in ppm | Kill rate in % after d found* | calc.** | d*** |
|---|---|---|---|---|
| (1-2) N-[2-(1,3-dimethylbutyl)phenyl]-5-fluoro-1,3-dimethyl-1H-pyrazole-4-carboxamide | 100 | 0 | | 6 |
| (6.2.1) fipronil | 100 | 65 | | 6 |
| (1-2) N-[2-(1,3-dimethylbutyl)phenyl]-5-fluoro-1,3-dimethyl-1H-pyrazole-4-carboxamide + (6.2.1) fipronil (1:1) | 100 + 100 | 85 | 65 | 6 |
| (1-2) N-[2-(1,3-dimethylbutyl)phenyl]-5-fluoro-1,3-dimethyl-1H-pyrazole-4-carboxamide | 100 | 0 | | 6 |

TABLE A-continued

| | | Kill rate in % after d | | |
|---|---|---|---|---|
| Active compounds | Active compound concentration in ppm | found* | calc.** | d*** |
| (3.1.1) methiocarb | 100 | 0 | | 6 |
| (1-2) N-[2-(1,3-dimethylbutyl)phenyl]-5-fluoro-1,3-dimethyl-1H-pyrazole-4-carboxamide + (3.1.1) methiocarb (1:1) | 100 + 100 | 25 | 0 | 6 |

*found = activity found
**calc. = activity calculated using Colby's formula
***d = evaluation after the given number of days Example B Phaedon cochleariae-Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, the following active compound combination in accordance with the present application showed a synergistically enhanced activity compared to the active compounds applied on their own:

TABLE B

Plant-damaging insects: *Phaedon cochleariae* - Test

| | | Kill rate in % after d | | |
|---|---|---|---|---|
| Active compounds | Active compound concentration in ppm | found* | calc.** | d*** |
| (1-2) N-[2-(1,3-dimethylbutyl)phenyl]-5-fluoro-1,3-dimethyl-1H-pyrazole-4-carboxamide | 100 | 0 | | 6 |
| (2.1.1) clothianidin | 0.8 | 0 | | 6 |
| (1-2) N-[2-(1,3-dimethylbutyl)phenyl]-5-fluoro-1,3-dimethyl-1H-pyrazole-4-carboxamide + (2.1.1) clothianidin (125:1) | 100 + 0.8 | 30 | 0 | 6 |
| (1-2) N-[2-(1,3-dimethylbutyl)phenyl]-5-fluoro-1,3-dimethyl-1H-pyrazole-4-carboxamide | 100 | 0 | | 6 |
| (2.1.2) imidacloprid | 0.8 | 40 | | 6 |
| (1-2) N-[2-(1,3-dimethylbutyl)phenyl]-5-fluoro-1,3-dimethyl-1H-pyrazole-4-carboxamide + (2.1.2) imidacloprid (125:1) | 100 + 0.8 | 80 | 40 | 6 |
| (1-2) N-[2-(1,3-dimethylbutyl)phenyl]-5-fluoro-1,3-dimethyl-1H-pyrazole-4-carboxamide | 100 | 0 | | 6 |
| (5.1.1) spinosad | 0.8 | 80 | | 6 |
| (1-2) N-[2-(1,3-dimethylbutyl)phenyl]-5-fluoro-1,3-dimethyl-1H-pyrazole-4-carboxamide + (5.1.1) spinosad (125:1) | 100 + 0.8 | 100 | 80 | 6 |
| (1-2) N-[2-(1,3-dimethylbutyl)phenyl]-5-fluoro-1,3-dimethyl-1H-pyrazole-4-carboxamid | 100 | 0 | | 4 |
| (3.1.2) thiodicarb | 100 | 0 | | 4 |
| (1-2) N-[2-(1,3-dimethylbutyl)phenyl]-5-fluoro-1,3-dimethyl-1H-pyrazole-4-carboxamide + (3.1.2) thiodicarb (1:1) | 100 + 100 | 20 | 0 | 4 |

*found = activity found
**calc. = activity calculated using Colby's formula
***d = evaluation after the given number of days

Example C

*Plutella xylostella*-Test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the diamond back moth (*Plutella xylostella*) while the leaves are still moist.

After the desired period of time, the kill in % is determined. 100% means that all caterpillars have been killed; 0% means that none of the caterpillars have been killed.

In this test, the following active compound combination in accordance with the present application showed a synergistically enhanced activity compared to the active compounds applied on their own:

TABLE C

Plant-damaging insects: *Plutella xylostella* - Test

| Active compounds | Active compound concentration in ppm | Kill rate in % after d found* | calc.** | d*** |
|---|---|---|---|---|
| (1-2) N-[2-(1,3-dimethylbutyl)phenyl]-5-fluoro-1,3-dimethyl-1H-pyrazole-4-carboxamide | 100 | 15 | | 6 |
| (2.1.1) clothianidin | 20 | 20 | | 6 |
| (1-2) N-[2-(1,3-dimethylbutyl)phenyl]-5-fluoro-1,3-dimethyl-1H-pyrazole-4-carboxamide + (2.1.1) Clothianidin (5:1) | 100 + 20 | 65 | 32 | 6 |
| (1-2) N-[2-(1,3-dimethylbutyl)phenyl]-5-fluoro-1,3-dimethyl-1H-pyrazole-4-carboxamide | 100 | 0 | | 6 |
| (2.1.2) imidacloprid | 4 | 20 | | 6 |
| (1-2) N-[2-(1,3-dimethylbutyl)phenyl]-5-fluoro-1,3-dimethyl-1H-pyrazole-4-carboxamide + (2.1.2) imidacloprid (25:1) | 100 + 4 | 40 | 20 | 6 |

*found = activity found
**calc. = activity calculated using Colby's formula
***d = evaluation after the given number of days

Example D

*Botrytis cinerea*-Test (In Vitro)/Microtitre Plates

The microtest is carried out in microtitre plates using potato dextrose broth (PDB) as liquid test medium. The active compounds are applied as technical-grade a.i., dissolved in acetone. A spore suspension of *Botrytis cinerea* is used for inoculation. After 5 days of incubation in the dark and with shaking (10 Hz), the transparency in each filled cavity of the microtitre plates is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is greater than the calculated activity, i.e. that a synergistic effect is present.

TABLE D

*Botrytis cinerea* - Test (in vitro)/microtitre plates

| Active compounds | Active compound concentration in ppm | Efficacy in % after d found* | calc.** | d*** |
|---|---|---|---|---|
| (1-2) N-[2-(1,3-dimethylbutyl)phenyl]-5-fluoro-1,3-dimethyl-1H-pyrazole-4-carboxamide | 3 | 16 | | 5 |
| (2.1.2) imidacloprid | 3 | 3 | | 5 |

TABLE D-continued

| | Botrytis cinerea - Test (in vitro)/microtitre plates | | | |
|---|---|---|---|---|
| | | | Efficacy in % after d | |
| | Active compound | | | |
| Active compounds | concentration in ppm | found* | calc.** | d*** |
| (1-2) N-[2-(1,3-dimethylbutyl)phenyl]-5-fluoro-1,3-dimethyl-1H-pyrazole-4-carboxamide + (2.1.2) imidacloprid (1:1) | 3 + 3 | 29 | 19 | 5 |

*found = activity found
**calc. = activity calculated using Colby's formula
***d = evaluation after the given number of days Example E Alternaria mali-Test (In Vitro)/Microtitre Plates The microtest is carried out in microtitre plates using potato dextrose broth PDB) as liquid test medium. The active compounds are applied as technical-grade a.i., dissolved in acetone. A spore suspension of Alternaria mali is used for inoculation. After 4 days of incubation in the dark and with shaking (10 Hz), the transparency in each filled cavity of the microtitre plates is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is greater than the calculated activity, i.e. that a synergistic effect is present.

TABLE E

| | Alternaria mali - Test (in vitro)/microtitre plates | | | |
|---|---|---|---|---|
| | | | Kill rate in % after d | |
| | Active compound | | | |
| Active compounds | concentration in ppm | found* | calc.** | d*** |
| (1-2) N-[2-(1,3-dimethylbutyl)phenyl]-5-fluoro-1,3-dimethyl-1H-pyrazole-4-carboxamide | 3 | 48 | | 4 |
| (2.1.1) clothianidin | 3 | 8 | | 4 |
| (1-2) N-[2-(1,3-dimethylbutyl)phenyl]-5-fluoro-1,3-dimethyl-1H-pyrazole-4-carboxamide + (2.1.1) clothianidin (1:1) | 3 + 3 | 58 | 53 | 4 |

*found = activity found
**calc. = activity calculated using Colby's formula
***d = evaluation after the given number of days

The invention claimed is:

1. A composition comprising a synergistic active compound combination, which comprises N-[2-(1,3-dimethylbutyl)phenyl]-5-fluoro-1,3-dimethyl-1H-pyrazole-4-carboxamide having the following formula:

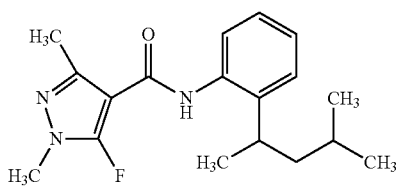

and one or more active compounds selected from the group consisting of
(2.1.1) clothianidin,
(2.1.2) imidacloprid,
(2.1.3) thiacloprid,
(2.1.4) thiamethoxam,
(2.1.5) acetamiprid,
(2.1.6) dinotefuran,
(2.1.7) nitenpyram,
nithiazine,
(3.1.1) methiocarb,
(3.1.2) thiodicarb,
benfuracarb,
carbosulfan,
(4.1.1) beta-cyfluthrin,
bifenthrin,
cypermethrin,
tefluthrin,
transfluthrin,
(5.1.1) spinosad,
(6.2.1) fipronil,
(6.2.2) ethiprole,
avermectin,
and
(21.1.1) $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide,
wherein the weight ratio of N-[2-(1,3-dimethylbutyl)phenyl]-5-fluoro-1,3-dimethyl-1H-pyrazole-4-carboxamide to said one or more active compounds is from 500:1 to 1:1000.

2. The composition according to claim 1, wherein the weight ratio of N-[2-(1,3-dimethylbutyl)phenyl]-5-fluoro-1,3-dimethyl-1H-pyrazole-4-carboxamide to said one or more active compounds is from 125:1 to 1:25.

3. The composition according to claim 1, wherein the weight ratio of N-[2-(1,3-dimethylbutyl)phenyl]-5-fluoro-1,3-dimethyl-1H-pyrazole-4-carboxamide to said one or more active compounds is from 125:1 to 1:50.

4. The composition according to claim 2, wherein said one or more active compounds are selected from the group consisting of clothianidin, imidacloprid, methiocarb, thiodicarb, spinosad and fipronil.

5. The composition according to claim 2, wherein said one or more active compounds are selected from the group consisting of beta-cyfluthrin, thiacloprid and $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide.

6. The composition according to claim 2, wherein said one or more active compounds are selected from the group consisting of acetamiprid, dinotefuran, nitenpyram, nithiazine, thiamethoxam, transfluthrin, tefluthrin, bifenthrin, cypermethrin, benfuracarb, carbosulfan, ethiprole and avermectin.

7. The composition according to claim 1, wherein said one or more active compounds are selected from the group consisting of dinotefuran, ethiprole, transfluthrin and $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide.

8. The composition of claim 1, wherein said one or more active compounds are selected from the group consisting of clothianidin, imidacloprid, thiacloprid, thiamethoxam, acetamiprid, dinotefuran and nitenpyram.

9. The composition of claim 1, wherein said one or more active compounds are selected from the group consisting of clothianidin and imidacloprid.

10. The composition of claim 1, wherein said one or more active compounds is dinotefuran.

11. A seed treated with the composition according to claim 1.

12. A seed treated with the composition according to claim 7.

13. A method for controlling unwanted pests and unwanted phytopathogenic fungi, comprising contacting said pests, fungi, or their habitat with the composition according to claim 1.

14. A method for controlling unwanted pests and unwanted phytopathogenic fungi, comprising contacting said pests, fungi, or their habitat with the composition according to claim 4.

15. A method for controlling unwanted pests and unwanted phytopathogenic fungi, comprising contacting said pests, fungi, or their habitat with the composition according to claim 5.

16. A method for controlling unwanted pests and unwanted phytopathogenic fungi, comprising contacting said pests, fungi, or their habitat with the composition according to claim 6.

17. A method for controlling unwanted pests and unwanted phytopathogenic fungi, comprising contacting said pests, fungi, or their habitat with the composition according to claim 7.

18. A method of treating transgenic plants, comprising contacting said plants with the composition according to claim 1.

19. A method for controlling insects, comprising contacting said insects or their habitat with the composition of any one of claims 8-10.

20. A method of treating seeds, comprising contacting said seeds with the composition according to claim 1.

21. The method according to claim 20, wherein said seeds are seeds of transgenic plants.

22. A method of treating seeds or transgenic plants, comprising contacting said seeds or said transgenic plants with the composition according to claim 4.

23. A method of treating seeds or transgenic plants, comprising contacting said seeds or said transgenic plants with the composition according to claim 5.

24. A method of treating seeds or transgenic plants, comprising contacting said seeds or said transgenic plants with the composition according to claim 6.

25. A method of treating seeds or transgenic plants, comprising contacting said seeds or said transgenic plants with the composition according to claim 7.

* * * * *